(12) United States Patent
Schlienger et al.

(10) Patent No.: US 8,066,706 B2
(45) Date of Patent: *Nov. 29, 2011

(54) SURGICAL NAIL

(75) Inventors: Andrè Schlienger, Münchenstein (CH); Markus Buettler, Oensingen (CH); Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 832 days.

This patent is subject to a terminal disclaimer.

(21) Appl. No.: 11/631,176

(22) PCT Filed: Jun. 30, 2004

(86) PCT No.: PCT/CH2004/000411
§ 371 (c)(1),
(2), (4) Date: Jun. 19, 2008

(87) PCT Pub. No.: WO2006/002551
PCT Pub. Date: Jan. 12, 2006

(65) Prior Publication Data
US 2008/0262496 A1 Oct. 23, 2008

(51) Int. Cl.
*A61B 17/56* (2006.01)
(52) U.S. Cl. ............... 606/64; 606/60; 606/62; 606/67
(58) Field of Classification Search ............ 606/62–68
See application file for complete search history.

(56) References Cited

U.S. PATENT DOCUMENTS

| 2,834,342 A | 5/1958 | Yost |
| 3,255,747 A | 6/1966 | Cochran et al. |
| 3,433,220 A | 3/1969 | Zickel |
| 4,095,591 A | 6/1978 | Graham, Jr. et al. |
| 4,103,683 A | 8/1978 | Neufeld |
| 4,172,452 A | 10/1979 | Forte et al. |

(Continued)

FOREIGN PATENT DOCUMENTS

CH 668 173 12/1988

(Continued)

OTHER PUBLICATIONS

International Search Report of PCT/CH2004/000411.

(Continued)

*Primary Examiner* — Eduardo C Robert
*Assistant Examiner* — Paul J Spatafore
(74) *Attorney, Agent, or Firm* — Fay Kaplun & Marcin, LLP

(57) ABSTRACT

A surgical nail (1), in particular, an intramedullary nail, has a central axis (2) and is formed of a material (M) having a modulus of elasticity (E). A plurality of transversal openings (5) run transversally to the central axis (2) and have a cross-sectional profile (F) and a transversal axis (6), the cross-sectional profile (F) having a maximum length (a) that runs in the direction of the central axis and a maximum width (b) that runs perpendicular to the length. A longitudinal bore (3) runs coaxially with the central axis (2) and defines a wall (4). A longitudinal insert (7) can be introduced into the region of the transversal opening (5) via the longitudinal bore (3). Said insert has a longitudinal axis (13) and consists of a material (m). The insert (7) comprises at least one longitudinal slot (25) so that said insert can be elastically compressed in a radial manner and includes a plurality of radial elevations (14) fitting inside the transversal openings (5).

23 Claims, 3 Drawing Sheets

U.S. PATENT DOCUMENTS

| | | | |
|---|---|---|---|
| 4,274,163 A | 6/1981 | Malcom et al. | |
| 4,438,762 A | 3/1984 | Kyle | |
| 4,494,535 A | 1/1985 | Haig | |
| 4,612,920 A | 9/1986 | Lower | |
| 4,621,628 A | 11/1986 | Brudermann | |
| 4,622,959 A | 11/1986 | Marcus | |
| 4,657,001 A | 4/1987 | Fixel | |
| 4,697,585 A | 10/1987 | Williams | |
| 4,705,027 A | 11/1987 | Klaue | |
| 4,754,749 A | 7/1988 | Tsou | |
| 4,776,330 A | 10/1988 | Chapman et al. | |
| 4,791,918 A | 12/1988 | Von Hasselbach | |
| 4,805,607 A | 2/1989 | Engelhardt et al. | |
| 4,817,591 A | 4/1989 | Klaue | |
| 4,858,602 A | 8/1989 | Seidel et al. | |
| 4,875,474 A | 10/1989 | Border | |
| 4,973,332 A | 11/1990 | Kummer | |
| 5,032,125 A | 7/1991 | Durham et al. | |
| 5,041,114 A | 8/1991 | Chapman et al. | |
| 5,041,115 A | 8/1991 | Frigg et al. | |
| 5,120,171 A | 6/1992 | Lasner | |
| 5,167,663 A | 12/1992 | Brumfield | |
| 5,176,681 A | 1/1993 | Lawes et al. | |
| 5,300,074 A | 4/1994 | Frigg | |
| 5,312,406 A | 5/1994 | Brumfield | |
| 5,364,398 A | 11/1994 | Chapman et al. | |
| 5,374,235 A | 12/1994 | Ahrens | |
| 5,454,813 A | 10/1995 | Lawes | |
| 5,484,439 A | 1/1996 | Olson et al. | |
| 5,549,610 A | 8/1996 | Russell et al. | |
| 5,569,249 A | 10/1996 | James et al. | |
| 5,573,536 A | 11/1996 | Grosse et al. | |
| 5,578,035 A | 11/1996 | Lin | |
| 5,591,168 A | 1/1997 | Judet et al. | |
| 5,653,000 A * | 8/1997 | Lee | 16/113.1 |
| 5,658,287 A | 8/1997 | Hofmann et al. | |
| 5,658,339 A | 8/1997 | Tronzo et al. | |
| 5,713,901 A | 2/1998 | Tock | |
| 5,713,902 A | 2/1998 | Friedl | |
| 5,728,099 A | 3/1998 | Tellman et al. | |
| 5,741,256 A | 4/1998 | Bresina | |
| 5,772,662 A | 6/1998 | Chapman et al. | |
| 5,908,422 A | 6/1999 | Bresina | |
| 5,928,235 A | 7/1999 | Friedl | |
| 5,935,127 A | 8/1999 | Border | |
| 5,976,139 A | 11/1999 | Bramlet | |
| 5,993,483 A * | 11/1999 | Gianotti | 623/1.22 |
| 6,010,506 A | 1/2000 | Gosney et al. | |
| 6,059,785 A | 5/2000 | Schavan et al. | |
| 6,106,528 A | 8/2000 | Durham et al. | |
| 6,123,708 A | 9/2000 | Kilpela et al. | |
| 6,126,661 A | 10/2000 | Faccioli et al. | |
| 6,187,007 B1 | 2/2001 | Frigg et al. | |
| 6,197,065 B1 | 3/2001 | Martin et al. | |
| 6,200,685 B1 | 3/2001 | Davidson | |
| 6,228,086 B1 | 5/2001 | Wahl et al. | |
| 6,261,290 B1 | 7/2001 | Friedl | |
| 6,292,979 B1 * | 9/2001 | Kuo | 16/113.1 |
| 6,296,645 B1 | 10/2001 | Hover et al. | |
| 6,443,954 B1 * | 9/2002 | Bramlet et al. | 606/62 |
| 6,454,810 B1 | 9/2002 | Lob | |
| 6,722,810 B1 * | 4/2004 | Tachikawa | 403/362 |
| 6,783,529 B2 * | 8/2004 | Hover et al. | 606/62 |
| 7,182,765 B2 | 2/2007 | Roth et al. | |
| 7,763,021 B2 * | 7/2010 | Cole et al. | 606/64 |
| 2002/0103488 A1 | 8/2002 | Lower et al. | |
| 2002/0151898 A1 | 10/2002 | Sohngen et al. | |
| 2002/0173792 A1 | 11/2002 | Severns et al. | |
| 2003/0069581 A1 | 4/2003 | Stinson et al. | |
| 2003/0114855 A1 | 6/2003 | Wahl et al. | |
| 2004/0006392 A1 * | 1/2004 | Grusin et al. | 623/19.14 |
| 2006/0064095 A1 | 3/2006 | Senn et al. | |
| 2006/0111716 A1 | 5/2006 | Schlienger et al. | |
| 2006/0149248 A1 | 7/2006 | Schlienger et al. | |
| 2006/0161155 A1 | 7/2006 | Schlienger et al. | |
| 2006/0189988 A1 | 8/2006 | Schlienger et al. | |
| 2006/0235395 A1 | 10/2006 | Frigg et al. | |
| 2006/0241605 A1 | 10/2006 | Schlienger et al. | |
| 2007/0125602 A1 * | 6/2007 | Marbach | 182/228.1 |

FOREIGN PATENT DOCUMENTS

| | | |
|---|---|---|
| CH | 668173 | 12/1988 |
| CH | 674 613 | 6/1990 |
| CH | 674613 | 6/1990 |
| DE | 196 29 011 | 1/1998 |
| DE | 196 29 011 A1 | 1/1998 |
| DE | 199 45 611 | 9/2001 |
| DE | 199 45 611 A1 | 9/2001 |
| DE | 103 20 855 | 2/2004 |
| EP | 0 251 583 | 1/1988 |
| EP | 0 251 583 A2 | 1/1988 |
| EP | 0 321 170 | 6/1989 |
| EP | 0 321 170 B1 | 6/1989 |
| EP | 0 381 462 | 8/1990 |
| EP | 0 381 462 A2 | 8/1990 |
| EP | 0 411 273 | 2/1991 |
| EP | 0 411 273 A1 | 2/1991 |
| EP | 0 471 418 | 2/1992 |
| EP | 0 471 418 A1 | 2/1992 |
| EP | 0 838 199 | 4/1998 |
| EP | 0 838 199 A1 | 4/1998 |
| EP | 0 845 245 | 6/1998 |
| EP | 0 845 245 A2 | 6/1998 |
| EP | 0 853 923 | 7/1998 |
| EP | 0 853 923 A1 | 7/1998 |
| EP | 0 882 431 A1 | 12/1998 |
| EP | 0 919 200 | 6/1999 |
| EP | 0 919 200 A1 | 6/1999 |
| EP | 0 968 685 A2 | 6/1999 |
| EP | 0 968 685 | 1/2000 |
| EP | 1 024 762 B1 | 8/2000 |
| EP | 1 053 718 | 11/2000 |
| EP | 1 053 718 A1 | 11/2000 |
| EP | 1 214 914 | 6/2002 |
| EP | 1 214 914 A2 | 6/2002 |
| EP | 1 260 188 | 11/2002 |
| EP | 1 260 188 A1 | 11/2002 |
| FR | 2 784 283 | 4/2000 |
| FR | 2 784 283 | 4/2002 |
| GB | 2 209 947 | 6/1989 |
| GB | 2209947 A | 6/1989 |
| JP | 09-066059 | 3/1997 |
| JP | 09-066060 | 3/1997 |
| JP | 09-066061 | 3/1997 |
| JP | 11-137566 | 5/1999 |
| JP | 2000-051224 | 2/2000 |
| JP | 2000-051224 | 2/2000 |
| JP | 2000-051225 | 2/2000 |
| JP | 2000-51225 | 2/2000 |
| JP | 2000-342596 | 12/2000 |
| WO | 93/15679 | 8/1993 |
| WO | WO 93/15679 | 8/1993 |
| WO | 96/15737 | 5/1996 |
| WO | WO 96/15737 | 5/1996 |
| WO | 97/37606 | 10/1997 |
| WO | WO 97/37606 | 10/1997 |
| WO | 98/05263 | 2/1998 |
| WO | WO 98/05263 | 2/1998 |
| WO | 98/30164 | 7/1998 |
| WO | WO 98/30164 | 7/1998 |
| WO | 98/41161 | 9/1998 |
| WO | WO 98/41161 | 9/1998 |
| WO | 98/46169 | 10/1998 |
| WO | WO 98/46169 | 10/1998 |
| WO | WO 99/20195 | 4/1999 |
| WO | WO 00/44946 | 8/2000 |
| WO | 00/67653 | 11/2000 |
| WO | WO 00/67653 | 11/2000 |
| WO | 02/060331 | 8/2002 |
| WO | WO 02/060331 | 8/2002 |
| WO | 03/015649 | 2/2003 |
| WO | WO 03/015649 | 2/2003 |

| | | |
|---|---|---|
| WO | WO 03/101320 | 12/2003 |
| WO | WO 2004/082494 | 9/2004 |

OTHER PUBLICATIONS

International Preliminary Examination Report for International Application No. PCT/CH04/00411, completed May 23, 2006, German language version.

International Preliminary Examination Report for International Application No. PCT/CH04/00411, completed May 23, 2006, English language translation of the German language version.

Wilkey et al., *Mechanical Characteristics of Eight Femoral Intramedullary Nailing Systems*, Journal of Orthopaedic Trauma, ISSN: 0890-5339, Mar./Apr. 1998, pp. 177-185, vol. 12, No. 3.

* cited by examiner

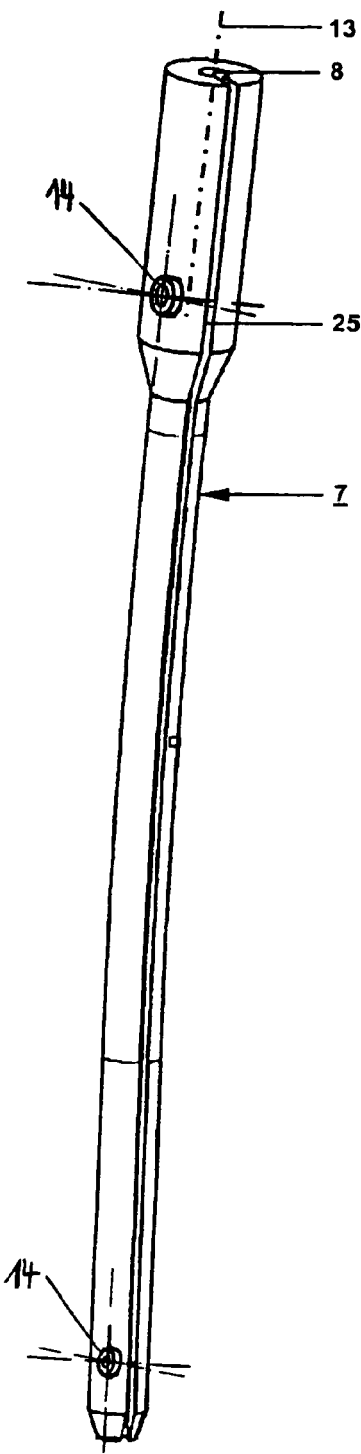
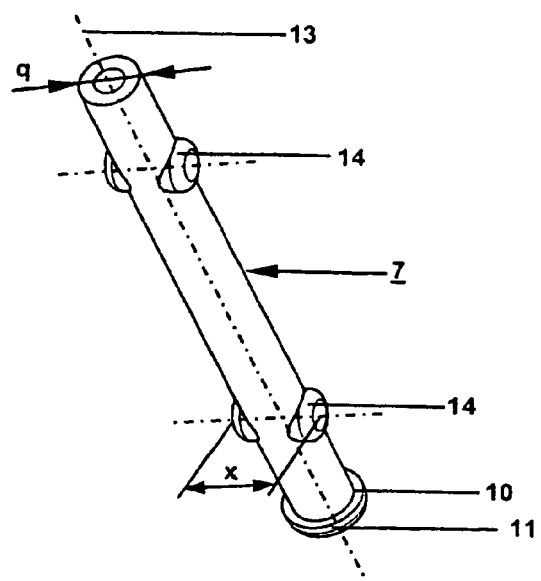
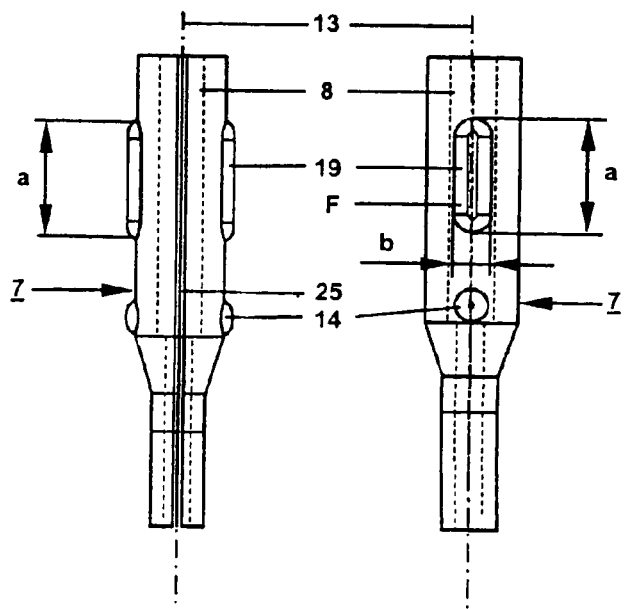

SURGICAL NAIL

RELATED APPLICATION DATA

This is the U.S. National Stage application of International Application No. PCT/CH2004/000411, filed Jun. 30, 2004.

FIELD OF THE INVENTION

The invention relates to a surgical nail, in particular an intramedullary nail for use in repairing bone fractures.

BACKGROUND OF THE INVENTION

The securing function of intramedullary nails is already known in the state of the art. The locking screws or locking pins (hereinafter only the term "locking screw" is used, but this is also intended to include the term other fasteners, such as locking pins) are inserted into the transverse bores in an intramedullary nail either with the help of an imaging method (x-ray monitoring) or a fairly complex targeting device. In both cases, a certain target inaccuracy is unavoidable, i.e., the tip of the screw cannot be aligned precisely coaxially with the central axis of the transverse bore but instead there is a certain deviation. In order for the locking screw to open into and pass through the transverse bore despite this target error, the outside diameter of the screw is undersized in relation to the diameter of the transverse bore. If the target inaccuracy remains within the scope of this undersizing, then the locking screw can be passed through the transverse bore with no problem despite this target error. However—because of the undersizing—the locking screw does have a certain amount of play in relation to the transverse bore.

This play defines the allowed amount of movement of the main bone fragments, which are to be secured in the corresponding locking hole by means of locking screws, in relation to the nail, and therefore, owing to the rigidity of the nail, also in relation to other main bone fragments attached with the same nail. This play is unavoidable in order to be sure that the surgeon will be able to use this locking means, but is nevertheless undesirable clinically for certain indications (e.g., in the case of metaphysical fragments).

Nails having a solid cross section, which may have an inside thread in the locking hole, are also not free of play. The inside thread only prevents the nail from being displaced axially on the locking screw.

US 2002/173792 (Hover et al.) describes a hollow intramedullary nail made of metal having one or two plastic inserts in the jacket openings in the transverse bore, which are positioned diametrically opposite one another and are referred to as windows, the locking screw being insertable through these plastic inserts. This known intramedullary nail has the disadvantage that the window-like plastic inserts are easily pushed in, causing the desired function to be lost. But even with very careful manipulation, the two plastic inserts could be forced out of their "windows" when the locking screw is passed through, which also causes a loss of function.

In a special embodiment of the Hover patent, an insert on the distal tip of the intramedullary nail that can be inserted into the central cavity thereof is provided in both windows in the transverse opening, but its material composition and function remain unclear.

SUMMARY OF THE INVENTION

The present invention seeks to remedy this situation. The object of the invention is to create a surgical nail, in particular an intramedullary nail, with which the play between the nail and the locking screw can be eliminated at no risk and an improved holding force between the locking screw and the intramedullary nail can be achieved without requiring the user to employ a high level of precision in performing the work. Another object is to create a surgical nail with an insert that can be inserted into its longitudinal bore and can also be introduced and aligned intraoperatively after insertion of the nail without applying any great force and without thereby reducing the holding force of the insert having been introduced.

The present invention achieves this object with a surgical nail formed of material with a first modulus of elasticity, the nail having a tubular body with a longitudinal central axis, a longitudinal bore extending along the axis between proximal and distal ends of the tubular body, and a transverse opening configured to receive a bone fastener. An elongated insert formed of material with a second, lower modulus of elasticity and configured to fit within the longitudinal bore in an installed position extends across the path of movement of a bone fastener through the transverse opening, the insert having a longitudinal slot enabling compression of the insert, and further having an elevation configured to project from the longitudinal bore into the transverse opening to locate the insert in the installed position.

The following advantages can be achieved in this way:

a) The insert is held axially in the longitudinal bore in the nail due to its radial initial stress;

b) The insert can be inserted into position without requiring any actual matching of play so that, for example, it is not necessary to maintain narrow tolerances as in the press fit;

c) The target accuracy in introducing the locking screw is unimpaired;

d) The nail and insert can be packaged separately in sterile packages and the surgeon can select whether to use the nail with or without the insert. If using the nail with the insert, the surgeon can insert the insert into the nail himself and optionally also remove it again. If the surgeon uses the nail without an insert, it still remains in the sterile package for the next use. The physician is thus able to decide intraoperative whether or not to use a stable-angle locking of the locking screw, where the term "stable angle" means a restriction of certain degrees of freedom; and e) The possibility of stable angle fixation of the bone fragment in certain directions for a certain amount of load;

f) Form-fitting locking of the insert in the longitudinal bore of the nail and thus an increased holding force in the longitudinal bore, which is also advantageous in extraction of the nail;

g) Ease of introduction and alignment of the insert intraoperatively and after insertion of the nail with the same advantages with regard to holding force;

h) The elevations on the insert optimize alignability and the holding force as well as retention of the insert in the cannulation in the event of extraction of the nail and i) The insert which has a longitudinal slot allows it to be inserted into the cannulated intramedullary nail because the projecting length of the elevations and the size of the diameter of the insert are radially flexible with a minor loss of holding power.

The insert is preferably designed in one piece. The longitudinal slot advantageously runs continuously over the entire length of the insert. The insert may also have multiple longitudinal slots that do not run over the entire length of the insert, so this results in increased stability of the insert. Furthermore, the longitudinal slots may also be arranged with an offset on the circumference of the insert, which results in an increased flexibility. The longitudinal slots may also be arranged axially one above the other.

In a special embodiment, at least one elevation is arranged in the same way as the at least one transverse opening and can be brought into engagement with the latter. The elevations corresponding to the transverse openings support the bracing effect of the locking screws in their installation.

The at least one elevation is preferably offset by 90° on the circumference of the insert in comparison with the at least one longitudinal slot. This yields the advantage that in radial compression of the insert, the elevations do not protrude beyond the diameter of the insert so that the latter can simply be pushed into the longitudinal bore in the nail. The height of the at least one elevation is preferably less than or equal to the width of the longitudinal slot.

The longitudinal slot preferably communicates with the longitudinal bore.

In a special embodiment, the nail has at least two transverse openings, preferably at least three transverse openings. In another embodiment the nail has at least two transverse openings in its distal half and at least two transverse openings in its proximal half.

A preferred further embodiment of the invention consists of the fact that the insert is designed in the form of a rod and can be inserted through the longitudinal bore in the nail up to the area of the transverse openings. The surgeon may also insert the insert after implantation of the nail (without insert) by advancing the insert from the proximal end into the longitudinal bore up to the area of the transverse openings.

The modulus of elasticity "e" of the insert is preferably "e"<0.8E and is typically "e"<0.7E.

In a special embodiment, the material m of the insert is a biocompatible plastic, preferably a polyethylene or a high molecular weight polyethylene (HMWPE). This has the advantage that there is no degradation of the plastic resulting in unknown degradation products.

In one alternative, the material introduced into the longitudinal bore in the hollow nail and having a lower hardness is a bioabsorbable plastic which is preferably a polylactide. In this embodiment, there is initially a play-free transverse locking of the intramedullary nail which is then canceled again successively with increasing absorption of the polymer so that the transverse locking screw becomes mobile again in relation to the intramedullary nail and thus also the bone fragments treated in this way. This allows a certain dynamic mobility of the bone fragments after successful fracture consolidation.

Another advantage of the bioabsorbable material is that chips formed in cutting of a thread by the locking screw through the nail can be absorbed by the body.

In another embodiment the nail has at least two transverse openings, preferably at least three transverse openings. The transverse opening preferably has a circular cross section, where a=b. However, the transverse opening may also be designed as an elongated hole having the cross-section profile F where the longer dimension "a" of the elongated hole is arranged in the axial direction of the nail.

The material "m" of the insert, preferably also has a lower density $\rho_1$ and the material M having the density $\rho_2$, whereby preferably $\rho_1 < 0.8\rho_2$.

The nail may comprise a locking screw or a locking pin insertable into the transverse opening (having the cross-sectional profile F) and through the insert, its outside thread and/or its unthreaded shaft having an outside diameter "d" which complies with the condition a>d<b.

In another embodiment the insert has a central longitudinal bore.

The diameter of the longitudinal bore of the nail in the direction of its central axis may be variable and the longitudinal bore may preferably have a circular shoulder.

In another embodiment the rod-shaped insert may also have a recess running radially across its longitudinal axis. Thanks to this recess, it is easier to center a locking screw or a locking pin and it is easier to drill through the insert, resulting in fewer chips of the material "m."

The insert may also have multiple recesses which are arranged in the same way as the transverse openings in the nail.

In another embodiment, the insert may be designed to be rod-shaped, preferably conical. Thanks to this shape, the insert is more easily inserted into the longitudinal bore of the nail from the distal end and furthermore a press fit is also possible.

In another embodiment the rod-shaped insert and the wall of the nail have cooperating means, preferably in the form of a groove and a matching elevation which secure the insert rotationally in a predetermined position in relation to the nail.

The elevations have a transverse extent "x" which is advantageously in the ratio 1<x/q<2 where "q" is the diameter of the insert. The advantage of this embodiment is that the elevations snap into the transverse openings on insertion of the insert into the longitudinal bore in the nail so that the insert is definitely and reliability positioned in the nail. The increased displacement volume also leads to an improved holding force, i.e., an increased angular stability.

The nail may already be made available to the surgeon with an insert already inserted into its longitudinal bore as far as the area of the transverse openings or alternatively they may be made available as separately packaged parts.

The nail may be used together with a locking screw having a screw shaft and an outside thread, whereby for the diameter d of the screw thread it holds that a>d<b, and "d" is preferably at least 5% smaller than the smaller of the two dimensions a, b.

In a special embodiment, the transverse openings are arranged in the distal half of the nail.

If the nail has only one transverse bore the insert may be inserted into the longitudinal bore into the area of this single transverse opening, but if the nail has two (or more) transverse bores, the insert may be inserted axially beyond the at least two transverse openings. Therefore a stable-angle fixation of the bone fragment is possible.

In another embodiment the insert is inserted axially beyond the at least two proximal transverse openings.

In a preferred embodiment, the insert has n≧2 elevations and the nail has N≧n, preferably N=n transverse openings in the area of the insert.

To manufacture the nail, a solid body made of a material "m" may be inserted into the longitudinal bore of the nail from the upper or lower end of the nail (made of the material M), so that the solid body comes to lie at least in the area of one of the transverse openings of the nail.

BRIEF DESCRIPTION OF THE DRAWINGS

The present invention and further embodiments of the invention are described in greater detail below on the basis of the partial schematic diagrams of multiple exemplary embodiments.

FIG. 12 shows a perspective view of an insert made of a biocompatible plastic for insertion from the distal end into a hollow intramedullary nail having radial elevations that secure its position rotationally according to the position of the transverse openings in the intramedullary nail;

FIG. 13 shows a side view through an insert made of a biocompatible plastic for insertion from the proximal end into a hollow intramedullary nail;

FIG. 14 shows a side view through the insert according to FIG. 13 rotated 90°;

FIG. 15 shows a view of a slotted insert for insertion from the proximal end over the entire length of the hollow intramedullary nail;

DETAILED DESCRIPTION OF THE PREFERRED EMBODIMENTS

Figure 1:
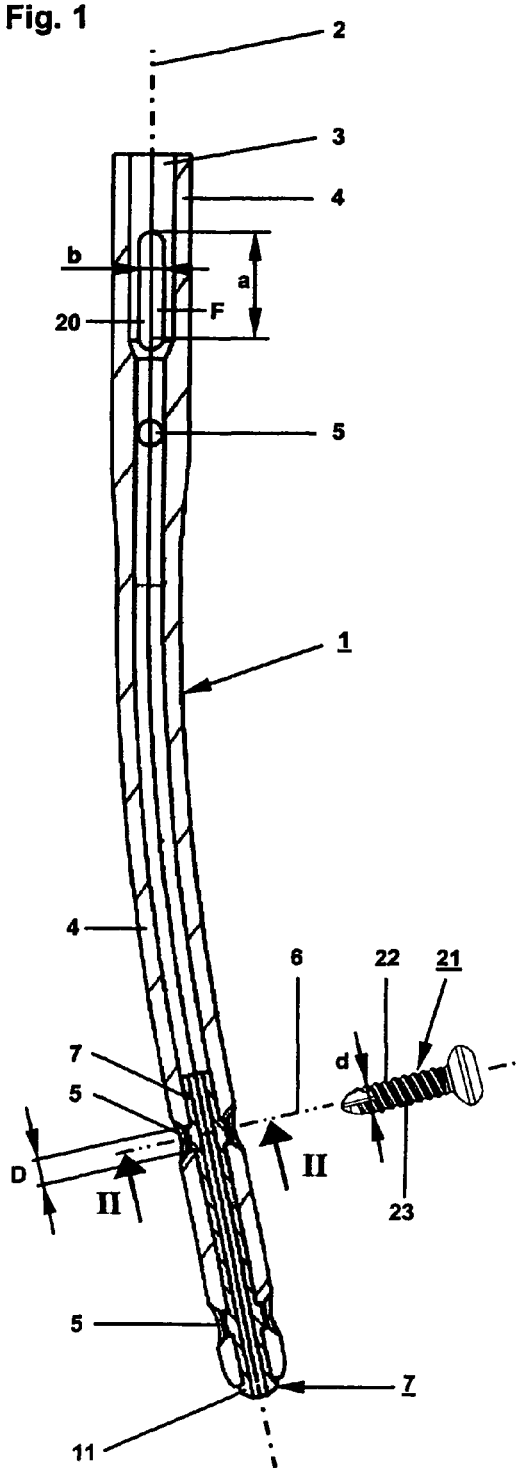
FIG. 1 shows a longitudinal section through a hollow intramedullary nail with radially elastically compressible slotted insert that has been inserted into it and a locking screw to be inserted into the transverse opening.

The surgical nail 1 shown in FIG. 1 is an intramedullary nail for tubular bones having a central axis 2 made of a material M (metal or metal alloy) and having three transverse openings 5 running across the central axis 2, the transverse opening having a diameter D and a transverse axis 6.

A fourth transverse opening is arranged proximally and is designed as an elongated hole 20, whereby the longer dimension is arranged in the axial direction. Two of the three transverse openings 5 are provided in the distal part of the intramedullary nail 1.

The intramedullary nail has a longitudinal bore 3 running coaxially with the central axis 2 and therefore a wall 4. A rod-shaped insert 7 (FIG. 2) in the form of a solid body made of absorbable polylactide is inserted into this longitudinal bore 3 from the distal end, resulting in the longitudinal bore 3 being filled with an accurate fit with a material m having a low strength, in particular a lower modulus of elasticity (in comparison with the material M of the intramedullary nail) in the area of the two distal transverse openings 5. However, a press fit of the material m is also possible.

As shown in FIG. 1, a locking screw 21 with the shaft 22 and the outside thread 23 may be screwed into the transverse opening 5 and thus also through the softer material of the insert 7.

Figure 2:
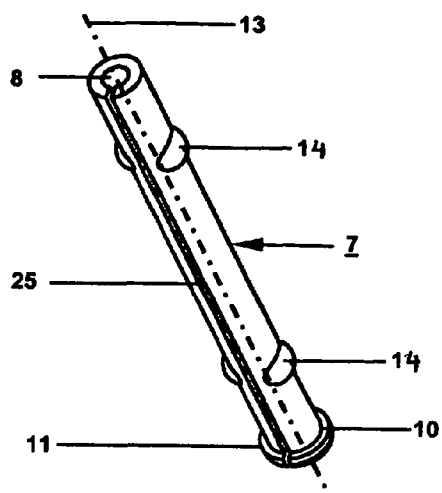
FIG. 2 shows a perspective view of the insert according to FIG. 1.
Figure 4:
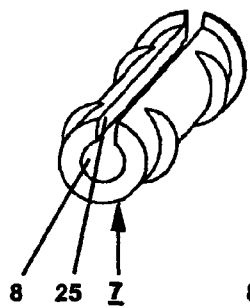
FIG. 4 shows a perspective view of an insert according to FIG. 2.
Figure 3:
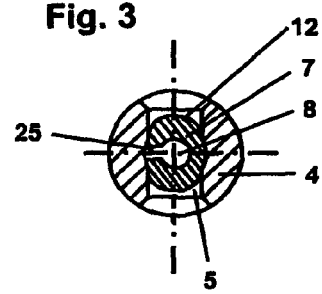
FIG. 3 shows a cross section through the insert along line II-II in FIG. 1.

As shown in FIGS. 2 through 4, the insert 7 has a longitudinal bore 8 running coaxially with its longitudinal axis 13 and communicating with a continuous longitudinal slot 25 running the entire length of the insert 7, so that the insert 7 is elastically compressible radially.

The insert 7 has on its distal end a hemispherical enlargement 11 with a stop 10 directed proximally. Secure axial positioning of the insert 7 in the longitudinal bore 3 of the intramedullary nail is ensured by the stop 10 of the enlargement 11. A hexagonal cavity 26 is provided in the hemispherical enlargement 11 to hold a hex head screwdriver. The insert also has a number of radial elevations 14—fitting into the transverse openings 5 in the nail 1.

Figure 5:
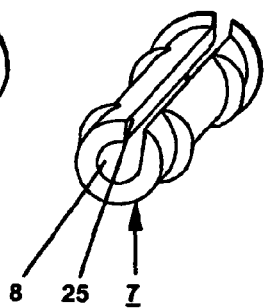
FIG. 5 shows a perspective view of another insert according to FIG. 2.

FIG. 5 shows a modified insert 7 in which the longitudinal slot 25 is arranged asymmetrically.

Figure 6:
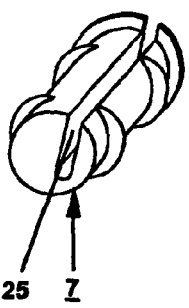
FIG. 6 shows a perspective view of another insert according to FIG. 2.
Figure 7:
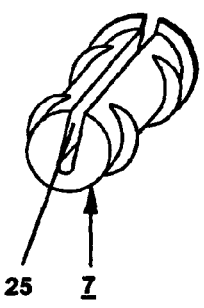
FIG. 7 shows a perspective view of another insert according to FIG. 2.

FIGS. 6 and 7 show other modified inserts 7 of which only one longitudinal slot 25 is provided instead of an actual longitudinal bore 8 with a longitudinal slot 25 opening to the outside; the longitudinal slot either runs next to the center (FIG. 6) or preferably cuts into the center of the insert (FIG. 7). Such a longitudinal slot 25 yields the desired radial elastic compressibility of the insert 7.

Figures 8, 9:
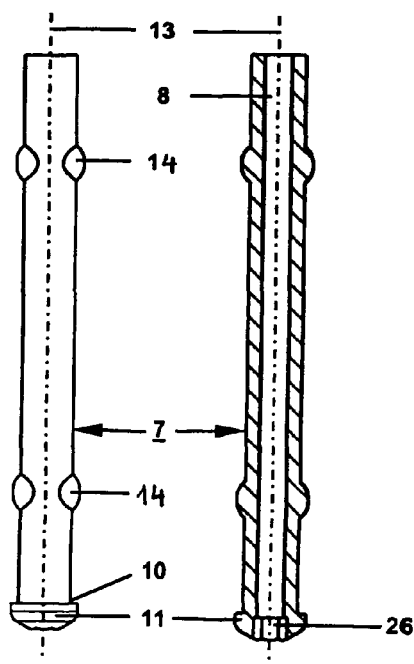
FIG. 8 shows a side view of the insert according to FIG. 2 made of a biocompatible material for insertion from the distal end into a hollow intramedullary nail having radial elevations and/or through-bores corresponding to the position of the transverse openings in the intramedullary nail.
FIG. 9 shows a longitudinal section through the insert according to FIG. 8.

The insert 7 shown in FIGS. 8 and 9 may be implemented in the form of a one piece solid body made of absorbable polylactide so that the longitudinal bore 3 in the nail 1 can be filled accurately with a material "m" of a lower strength, in particular a lower modulus of elasticity "e" (in comparison with the material M and/or the modulus of elasticity E of the intramedullary nail) with an accurate fit in the area of the two distal transverse openings 5. However, a press fit of the material m is also possible.

Figure 10:
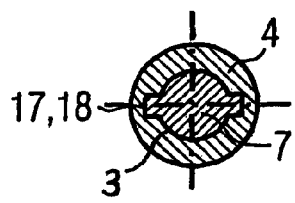
FIG. 10 shows a cross section through the intramedullary nail in the area of the transverse opening with an insert that has been inserted and aligned therein.

As shown in FIG. 10, the fully lined insert 7 and the longitudinal bore 3 of the intramedullary nail may have two ribs/grooves 17, 18 which prevent rotation.

Figure 11:
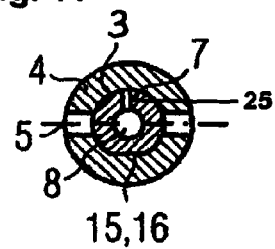
FIG. 11 shows a cross section through the intramedullary nail in the area of the transverse opening with an insert that has been inserted therein and secures the position rotationally.

As shown in FIG. 11, the insert 7 having a longitudinal bore 8 and a longitudinal slot 25 and the longitudinal bore 3 of the intramedullary nail may have profiles 15, 16 in the form of flattened faces which also have the effect of blocking rotation. Profiles 15, 16 as well as the ribs/grooves 17, 18 run over only a portion of the front end of the insert 7.

FIG. 12 shows another insert 7 on which the radial elevations 14 can snap into the openings of the transverse openings 5 in the wall 4 of the nail 1 thanks to their elasticity, so that the insert 7 can be secured both axially and rotationally. The transverse extent x of the elevations 14 is in a ratio $1<x/q<2$ where q is the diameter of the insert 7.

FIGS. 13 and 14 show a slotted insert 7 which can be inserted into the longitudinal bore 3 of the intramedullary nail 1 from the proximal end instead of from the distal end. It has an axial longitudinal bore 8 and an elevation 19 corresponding to the elongated hole 20 (with the cross-sectional profile F with the length a and width b) in the intramedullary nail 1. The elevation 19 corresponds approximately to the geometry of the elongated hole 20.

FIG. 15 shows another embodiment of an insert 7 which has approximately the same length as the intramedullary nail 1 and thus covers all the transverse openings 5 (locking bores) of the intramedullary nail 1 from proximal to distal ends. The insert 7 has a continuous longitudinal bore 8 and a longitudinal slot 25. An elevation 14 is provided on the distal portion and another on the proximal portion of the insert 7. The insert 7 may also be shortened intraoperatively as needed.

Figure 17:
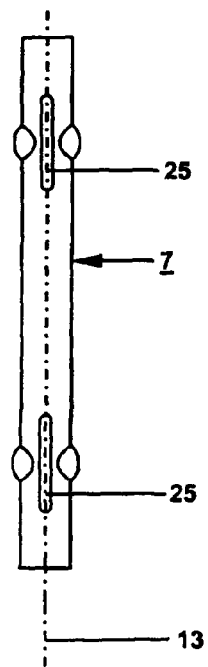
FIG. 17 shows a side view of the insert according to FIG. 16.
Figure 16:
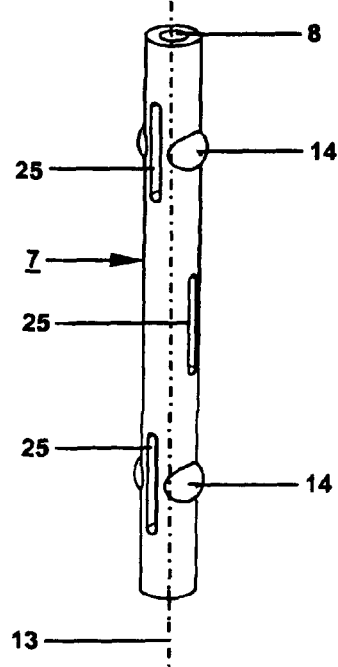
FIG. 16 shows a perspective view of an insert provided with a plurality of longitudinal slots arranged with a radial offset.

FIGS. 16 and 17 show another alternative of the insert 7 which also has a longitudinal bore 8 and elevations 14. This insert also has several longitudinal slots 25 arranged with a radial offset.

The invention claimed is:

1. An apparatus comprising:
a surgical nail formed of material with a first modulus of elasticity, the nail having a tubular body with a longitudinal central axis, a longitudinal bore extending along the axis between proximal and distal ends of the tubular body, and a first transverse opening configured to receive a bone fastener; and
an elongated insert formed of material with a second, modulus of elasticity lower than the first modulus of elasticity, the insert including a body sized and shaped to be inserted along the longitudinal central axis and through the longitudinal bore in an installed position, a first protrusion extending laterally from the body and configured to extend into the first transverse opening when the insert is in the installed position within the nail, the insert further including a longitudinal slot extending along the body to permit radial compression of the insert during insertion into the nail so that, when the insert is in the desired position, frictional engagement between the insert and the nail maintains the insert in the desired position, and further comprising a bone fastener sized and shaped to be received within the first transverse opening in the tubular body, the bone fastener having a shaft with a cross sectional size smaller than the cross sectional size of the first transverse opening.

2. The apparatus of claim 1, wherein the first transverse opening has a circular cross section.

3. The apparatus of claim 1, wherein the insert is one piece.

4. The apparatus of claim 1, wherein the longitudinal slot extends the full length of the insert.

5. The apparatus of claim 1, wherein the longitudinal slot is one of a plurality of longitudinal slots that extend only partly along the length of the insert.

6. The apparatus of claim 5, wherein at least two of the slots are offset from each other about the periphery of the insert.

7. The apparatus of claim 6, wherein at least two of the slots are spaced axially from each other.

8. The apparatus of claim 1, wherein the first protrusion is configured to snap into the first transverse opening in the tubular body upon movement of the insert into the installed position in the longitudinal bore.

9. The apparatus of claim 1, wherein the first protrusion is offset from the longitudinal slot 90° about the periphery of the insert.

10. The apparatus of claim 1, wherein the height of the first protrusion is no greater than the width of the longitudinal slot.

11. The apparatus of claim 1, wherein the insert has a longitudinal bore that is coaxial with the longitudinal bore in the tubular body when the insert is in the installed position.

12. The apparatus of claim 1, wherein the nail further includes a second transverse opening aligned with the first transverse opening so that the bone fastener inserted through the nail via the first transverse opening enters the second transverse opening.

13. The apparatus of claim 12, wherein the first and second transverse openings are located in a proximal half of the tubular body, the nail further including third and fourth transverse openings located in a distal half of the tubular body.

14. The apparatus of claim 1, wherein the insert is rod shaped.

15. The apparatus of claim 1, wherein the insert has a conical section configured to fit within a conical section of the longitudinal bore in the tubular body.

16. The apparatus of claim 1, wherein the tubular body and the insert together define a tongue and groove for restraining rotation of the insert relative to the tubular body.

17. The apparatus of claim 1, wherein the first transverse opening is located in a distal half of the tubular body.

18. The apparatus of claim 12, wherein the insert extends axially past the first and second transverse openings in the tubular body when in the installed position.

19. The apparatus of claim 18, wherein the first and second transverse openings are located in a proximal half of the tubular body.

20. The apparatus of claim 12, wherein a number of protrusions formed on the body is no greater than a number of transverse openings formed in the nail.

21. The apparatus of claim 1, wherein the first transverse opening in the tubular body and the first protrusion on the insert have elongated shapes.

22. The apparatus of claim 12, wherein the first protrusion extends around a portion of the insert on a first side of the slot and a second protrusion extends around a portion of the body on a second side of the slot so that. in the installed position, the first and second protrusions project into the first and second transverse openings, respectively, on opposite sides of the longitudinal bore.

23. The apparatus of claim 22, wherein the first protrusion extends from a first end attached to the body to a second end and the second protrusion extends from a third end attached to the body to a fourth end, a distance between the second and fourth ends being no more than two times a diameter of the body of the insert.

* * * * *